(12) United States Patent
Hecht et al.

(10) Patent No.: US 6,245,938 B1
(45) Date of Patent: *Jun. 12, 2001

(54) 4-PENTENOYL GROUPS FOR DERIVATIZATION AND PROTECTION OF AMINO ACIDS

(75) Inventors: Sidney Hecht; Michiel Lodder, both of Charlottesville, VA (US)

(73) Assignee: University of Virginia Patent Foundation, Charlottesville, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/970,615

(22) Filed: Nov. 14, 1997

Related U.S. Application Data

(60) Provisional application No. 60/030,954, filed on Nov. 15, 1996.

(51) Int. Cl.⁷ .......................... C07E 229/30; C07B 55/00
(52) U.S. Cl. .......................... 562/441; 562/401; 562/442; 562/450; 562/452; 562/454; 562/455
(58) Field of Search ................... 562/441, 442, 562/452, 450, 454, 455, 401

(56) References Cited

U.S. PATENT DOCUMENTS 6,093,831 * 7/2000 Rapoport et al. ............... 548/227

OTHER PUBLICATIONS

Database CAPLUS on STN, Acc. No. 1985:406670, Stierl et al., 'Use of selective amide cleavage for resolution of amino acid racemates.' Chimia (1984), 38(12) pp. 432–435 (abstract)., 1985.*

J. Biol. Chem., 1955, pp. 39, 213.
J. Pharm. Sci., 1978, P. 520
J. Org. Chem., 1992, pp. 57, 6286.
J. Chem. Soc., 1962, P. 3963.
Monatsh. Chem., 1954, P. 1060.
J. Med. Chem., 1992, P. 1897.
J. Pharm. Sci., 1978, pp. 67, 520.
Tet. Lett., 1986, pp. 27, 6079.
Tet. Lett., 1989, pp. 30, 4019.
Jacs, 1989, pp. 111, 6354.
J. Org. Chem., 1993, pp. 58, 683.
Helv. Chim. Acta., 1992, P. 2572.
Database CAPLUS on STN, Acc. No. 1987:497086, Lee et al., 'Conversion of serine beta–lactones to chiral alpha–amino acids by copper–containing organolithium and organomagnesium reagents.' J. Am. Chem. Soc. (1987), 109(15), p4649–59, abstract.*
Roesser et al., S.M. Biochemistry 28:5185 (1989).*
Robertson et al., J. Am Chem. Soc. 113:2722 (1991).*
Baldini et al. J. Biochemistry 27:7959 (1988).*

* cited by examiner

Primary Examiner—Gary Geist
Assistant Examiner—Brian J. Davis

(57) ABSTRACT

A method of separating a racemic mixture of amino acid enantiomers, which entails reacting the mixture with a 4-pentenoyl compound, thereby derivatizing the enantiomers to form two diastereomers, and separating the diastereomers.

19 Claims, 3 Drawing Sheets

4-PENTENOYL GROUPS FOR DERIVATIZATION AND PROTECTION OF AMINO ACIDS

This application is a regular National application claiming priority from Provisional Application, U.S. application Ser. No. 60/030,954 filed Nov. 15, 1996.

BACKGROUND OF THE INVENTION

1. Field of the Invention

This invention pertains to protecting groups suitable for the protection of aminoacylated peptide moieties used to prepare misacylated tRNA's and to derivatize amino acids so as to facilitate the recovery of optically pure compounds. A family of compounds based on the 4-pentenoyl group, which forms a stable bound with the $N^\alpha$ site of amino acids has proved suitable for use both as a protecting group, and a derivatizing group for the optical separation of enantiomers. N-substituted 2-amino 4-pentenoyl derivatives are obtained, and can be used for the preparation of misacylated tRNA. Such suppressor tRNA can be used to elaborate proteins with synthetic amino acids at predetermined sites. In particular, N-substituted 2-amino-4-pentenoyl derivatives can be used for this process. The protecting group, if so used, is easily removed by treatment with iodine, with respect to which the protected amino acid and biologically effective groups in general are stable.

2. Background of the Prior Art

In recent years, the elaboration of proteins containing synthetic amino acids at predetermined sites has become technically feasible; the strategy employed involves readthrough of nonsense codons, Noren, et al., P.G. Science 244:182 (1989) with misacylated suppressor tRNA's. Hecht, et al., S.J. Biol. Chem. 253:4517 (1978). As first shown by Hecht and coworkers, Heckler, et al., S.M. J. Biol. Chem. 258:4492 (1983), Heckler, et al., S.M. Biochemistry 23:1468 (1984), misacylated tRNA's are accessible by T4 RNA ligase-mediated coupling of aminoacylated pCpA derivatives with tRNA's from which the 3'-terminal dinucleotide has been removed (FIG. 1).

While T4 RNA ligase-mediated ligation has been effected using unprotected aminoacyl-pCpA derivatives, Baldini, et al., J. Biochemistry 27:7959 (1988), the lability of the aminoacyl moiety has led most workers to employ amino acid protecting groups that impart chemical stability. Although numerous groups have been described in the literature as amine protecting groups, Greene, et al., Protecting Groups in Organic Synthesis $2^{nd}$ Ed., John Wiley and Sons, New York, (1991), relatively few are suitable for the protecting of aminoacyl-pCpA derivatives. Almost none of the reported groups can be removed under conditions compatible with the integrity of the derived aminoacyl-tRNA's. The most satisfactory ones reported to date have been the pyroglutamyl Roesser, et al., S.M. Biochemistry 28:5185 (1989), and the nitroveratryloxycarbonyl (NVOC) Robertson, et al., J. Am. Chem. Soc. 113:2722 (1991) groups, removable by enzymatic proteolysis and photolytic cleavage, respectively. Baldini, et al. J. Biochemistry 27:7959 (1988). No protecting group removable with facility by a simple chemical treatment has been reported. Mendel, et al. J. Am. Chem. Soc. 113:2758 (1991).

Another problem, frequently encountered, in the synthesis of misacylated suppressor tRNA's is the chirality of the amino acids. Most interesting unnatural amino acids are obtained as racemic mixtures, or at best in an enantiomeric excess of one of the optical isomers. Some interesting methods for the asymmetric synthesis of amino acids have been developed, Williams, R. M., Synthesis of Optically Active α-Amino Acids Pergamon, Oxford, (1989), but few are stereospecific and most require additional separation in order to obtain optically pure derivatives.

Accordingly, it continues to be an object of those of skill in the art to provide and to address these problems we sought a group that would be suitable for the protection of $N^\alpha$ of aminoacyl-pCpA derivatives and at the same time would allow us to obtain optically pure derivatives.

SUMMARY OF THE INVENTION

The invention provides N-substituted 2-amino-4-pentenoyl derivatives which are effective in separating racemic mixtures of amino acids, which derivatizing groups can be further used as protecting group during manipulations of the optically active amino acids. In particular, bulky substituents on the amino group improve separation facility, without hindering the protection. Optically pure (L or D) 2-amino-4-pentenoyl acid derivatives, reacted with racemic mixtures, lead to separation of diastereomers by convenient methods. In particular, N-phenylfluorenyl-L-2-amino-4-pentenoyl and the bulkier N-benzyl-N-phenylfluorenyl-L-2-amino-4-pentenoic acid give particularly preferred results. The inventive compounds are represented by a compound of the formula I:

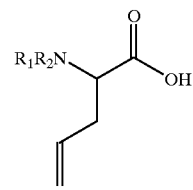

I wherein $R_1$ is a moiety Y selected from the group consisting of aryl, aryloxy, carboxy, carbonyl, alkoxy, cyclic alkyl, fused and unfused polycylic compounds including aryl rings, alkyl rings and aryl and alkyl rings, said moiety Y being of 6–30 carbon atoms, and when $R_2$ is independently a moiety Y or H, wherein $R_1$ and $R_2$ taken together are sufficiently bulky so as to permit separation by chromatography of two diastereomers found by derivatizing enantiomers of a racemic mixture with said compound of formula I.

DETAILED DESCRIPTION OF THE INVENTION

Figure 1:
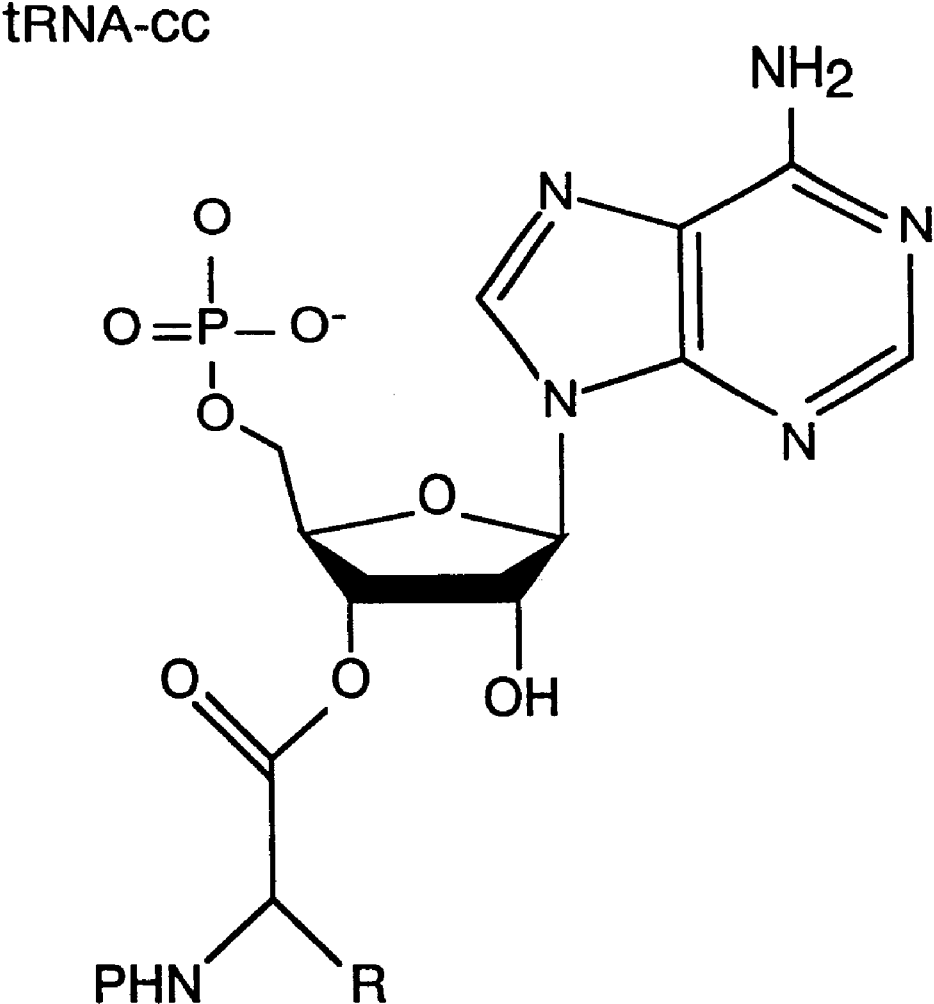
FIG. 1 is an illustration of a misacylated tRNA from which the 3'-terminally dinucelotide has been removed.

In order to solve the problem of the protecting of aminoacyl-pCpA derivatives we explored several amine protecting groups. Unexpectedly, the 4-pentenoyl group Debenham, et al. Org. Chem. 60:7920 (1995), proved to be suitable for the elaboration of misacylated suppressor tRNA's. This group forms a stable amide bond with $N^\alpha$ of amino acids and stabilizes the aminoacyl-pCpA derivatives during T4 RNA ligase-mediated aminoacyl-tRNA synthesis. The use of aqueous iodine for the deblocking of the pentenoyl group is compatible with the structure of the intermediates and does not cause any degradation of the derived aminoacyl-tRNA's.

Encouraged by the efficient deprotection of the pentenoyl group we set out to investigate the possibilities of utilizing derivatives of this group for the synthesis of optically pure compounds. An effective way of separating racemic amino acids is by indirect enantioseparation. Lindner, et al. Cromatographic Chiral Sepcarations, page 91 (1988). This technique uses chiral derivatizing reagents to convert the enantiomers into diastereomers, which can be separated based on their different physical properties. Although many derivatizing reagents are known, Lindner, et al. Cromatographic Chiral Sepcarations, page 91 (1988), Skidmore, et al. Handbook of Derivatives for Chromatogrphy, page 215 (1993) most cannot be removed from the optically pure compounds after separation and are only useful for analytical purposes. We reasoned that a chiral pentenoyl derivative would have the required properties for separation and still could be removed under the mild conditions of treatment with aqueous iodine. Preliminary results from systematic variations on the pentenoyl group and literature precedents Cardiollo, et al., Tetrahedron Lett. 27:6079 (1986) on halolactonization reactions showed that additional substituents should not have adverse effects on the deprotection reaction.

We focused our attention on the 2-amino-4-pentenoyl group. This compound has a chiral center close to the formed amide bond and provides the opportunity to introduce bulky substituents on the chiral center, necessary for enantioseparation. Lindner, et al. Chromatographic Chiral Separations, page 91 (1988), Skidmore, et al. Handbook of Derivatives for Chromatogrphy, page 215 (1993). In order to study the effect of N-substituents on the deprotection reaction we synthesized several N-substituted 2-amino-4-pentenoyl derivatives. As shown in Scheme 1, presented at the end of this Specification, N-benzyloxycarbonyl 2-amino-4-pentenoic acid (3) was made from glycine derivative 1. Thus, allyl ester 2 was made from N-benzyloxycarbonyl glycine (1) and converted to compound 3 by an ester enolate Claisen rearrangement. Kazmaier et al. Chem. Int. Ed. Engl. 34:2012 (1995). L-Valine benzyl ester Zervas, et al., J. Org. Chem. 22:1515 (1957). was coupled to 3 by a DCC-HOBt coupling to give compound 4. Treatment with iodine in aqueous THF afforded L-valine benzyl ester (5) in reasonable yield. Starting from commercially available 2-amino-4-pentenoic acid (6) N-butyloxycarbonyl derivative 7 was made (Scheme 2, presented at the end of this Specification). Compound 7 was also coupled to L-valine benzyl ester to give 8 and amine 5 was retrieved upon treatment with aqueous iodine. Next, phenylfluorenyl Christie, et al., J. Org. Chem. 50: 1239 (1985) was introduced as a bulky N-substituent (Scheme 3, presented at the end of this Specification). 2-Amino-4-pentenoic acid (6) was treated with 9-bromo-9-phenylfluorene to afford compound 9, which was attached to L-valine benzyl ester to give 10. A reaction of compound 10 with iodine in aqueous THF yielded, in addition to amine 5, iodolactone 11, proving that the deprotection reaction proceeds in the same fashion for the unsubstituted pentenoyl group.

Figure 2:
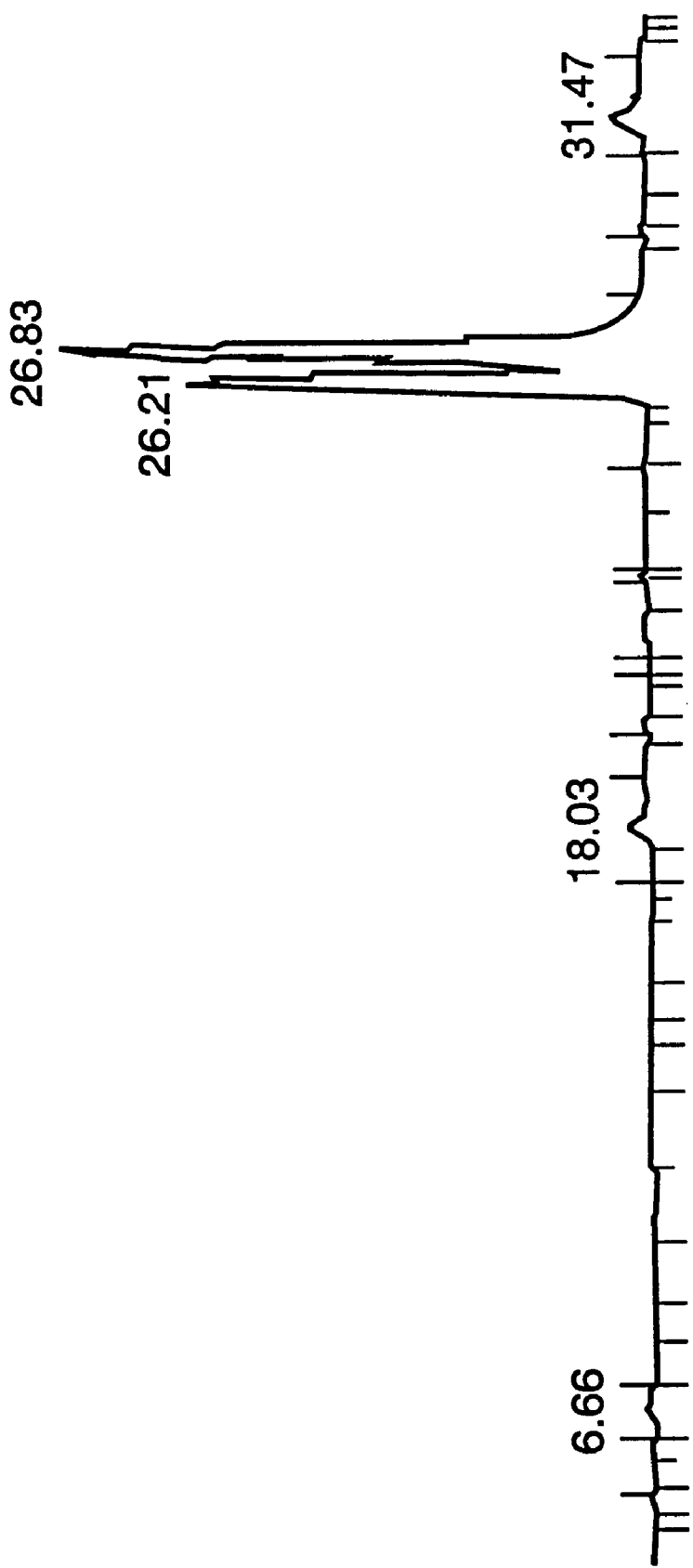
FIG. 2 is the illusion chart, on a silica column, of diastereomers derivatized with N-phenylfluorenyl-L-2-amino-4-pentenoic acid.

In order to investigate the possibility of utilizing this compound for the separation of racemic amino acids, chiral protecting group 13 was made (Scheme 4). Attachment of the phenylfluorenyl group to L-2-amino-4-pentenoic acid (12) gave optically pure 13, which was coupled to racemic phenylalanine benzyl ester Zervas, et al., J. Org. Chem. 22:1515 (1957), affording a mixture of diastereomers 14 and 15. Analysis of the mixture showed that it was possible to separate the diastereomers by normal phase HPLC (FIG. 2). Coinjection with optically pure 15, derived form L-phenylalanine benzyl ester, showed that the diastereomer derived from the D-amino acid eluted first, followed by the one derived from the L-amino acid.

Although we achieved our goal of separating racemic amino acids by derivatization with a chiral pentenoyl derivative, we set out to improve the separation efficiency of the derivatizing reagent. Use of the N-phenylfluorenyl-L-2-amino-4-pentenoyl group required HPLC separation, which can be a limiting factor for the utilization of this group in preparative synthesis. It was thought that a combination of the N-phenylfluorenyl group with an additional N-substituent would increase the steric hinderance, Humphrey, et al., J. Org. Chem. 59:2467 (1994), and therefor would increase the physical differences between the diastereomers. N-Benzyl-N-phenylfluorenyl-L-2-amino-4-pentenoic acid (21) was made from L-2-amino-4-pentenoic acid (12) in 6 steps (Scheme 5). Compound 12 was protected with a butyloxycarbonyl group and subsequently converted to o-nitrobenzyl ester 17. The amine protecting group was removed and the benzyl group was introduced by reductive amination, followed by the phenylfluorenyl group, affording compound 20. Photochemical Patchornik, et al., J. Am. Chem. Soc. 92:6333 (1970), cleavage of the o-nitrobenzyl ester gave N-disubstituted pentenoyl derivative 21.

Figure 3:
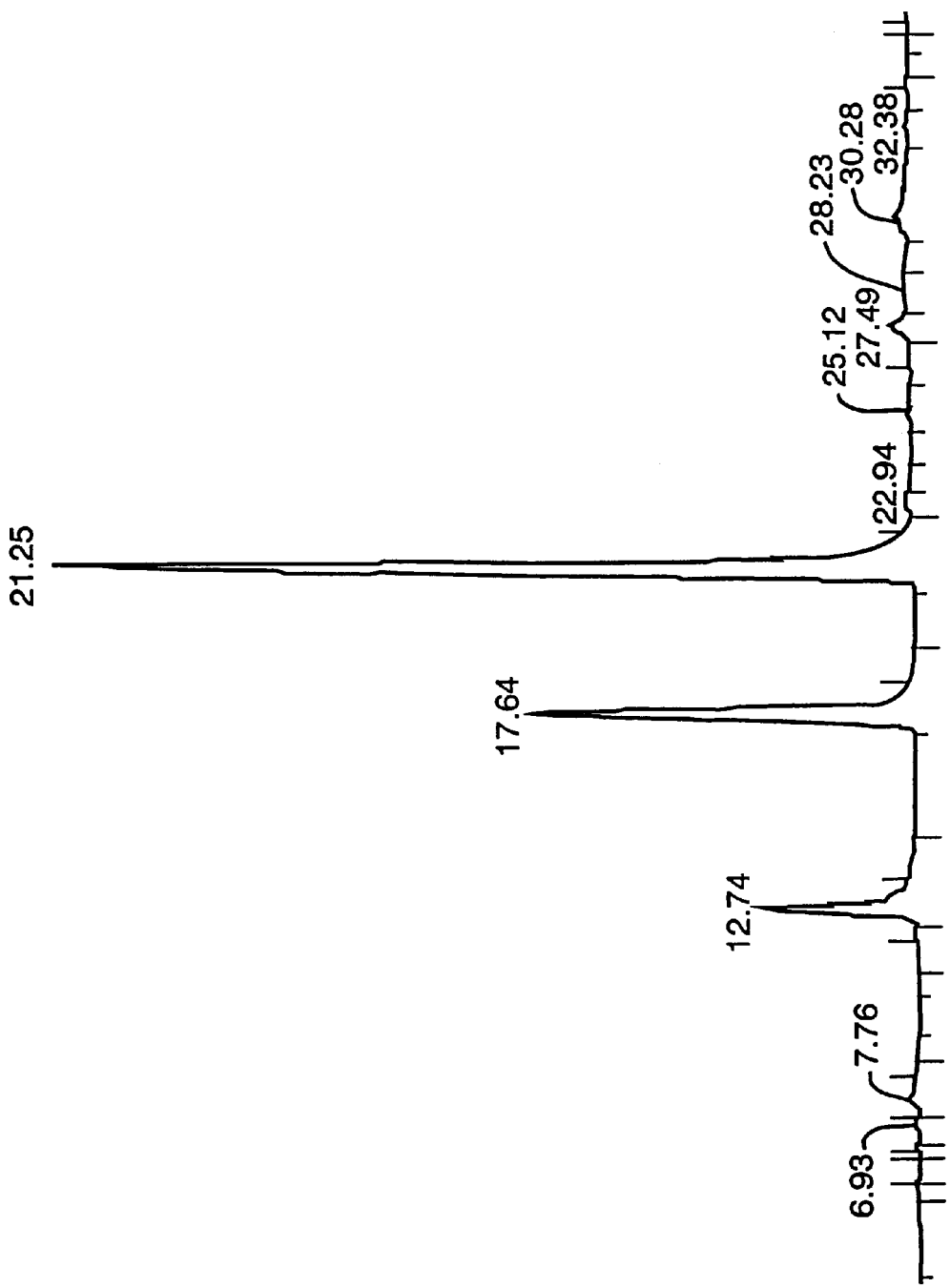
FIG. 3 is an illusion chart reflecting the separation of diastereomers of L-valine benzyl ester derivatized with N-benzyl-N-phenylfluorenyl-L-2-amino-4-pentenoic acid.

N-Benzyl-N-phenylfluorenyl-L-2-amino-4-pentenoic acid (21) was utilized as a derivatizing reagent in the separation of racemic amino acids. Coupling of 21 with racemic L-valine benzyl ester gave a mixture of diastereomers 22 and 23, which were separated by open column chromatography (Scheme 6). Elution of a silica gel column with 4:1 hexanes-ethyl acetate afforded optically pure 22 and 23 in a 1:2 ratio. HPLC analysis of the crude reaction mixture showed much better separation than in case of compounds 14 and 15 (FIG. 3). Comparison of the mixture of diastereomers with pure compounds 22 and 23, derived from D- and L-valine benzyl ester, respectively, showed that the diastereomer derived from the D-amino acid eluted first at 17.6 min, followed by the diastereomer derived from the L-amino acid at 21.3 min. Furthermore, the ratio of 1:2 in which the compounds were obtained implies that there is a preference for the naturally occurring L-amino acid in the coupling reaction with compound 21.

N-substituted 2-amino-4-pentenoyl derivatives can be used for the separation of racemic amino acids. The derivatizing reagent can be removed by treatment with aqueous iodine after separation or can be used as a protecting group during further manipulations of the optically active amino acids. The N-benzyl-N-phenylfluorenyl-L-2-amino-4-pentenoyl group is especially useful for the synthesis of chirally pure compounds, because the separation of the diastereomers does not rely on HPLC chromatography. Furthermore, the mild conditions employed for the removal of the group are compatible with the integrity of aminoacyl-tRNA's, which makes it possible to utilize this strategy for the synthesis of N-protected aminoacyl-pCpA derivatives.

Experimental Procedure

N-Benzyloxycarbonyl Glycine Allyl Ester (2) To a solution of 209 mg (1 mmol) N-benzyloxycarbonyl glycine (1) in 3 mL ethyl acetate was added 2 mL (1 mmol) of a 0.5 N solution of cesium carbonate in $H_2O$. The mixture was stirred for 30 min, 5 mL DMF was added and the solvent removed under diminished pressure. This was repeated twice to ensure the removal of $H_2O$. The residue was dissolved in 5 mL DMF and 100 μL (1.15 mmol) allylbromide was added. The reaction was stirred for 17 h and DMF was removed under diminished pressure. The residue was dissolved in 10 mL $CH_2Cl_2$ and washed with two 10-mL portions of saturated $NaHCO_3$ and with 10 mL brine. The organic layer was dried ($MgSO_4$) and concentrated to afford N-benzyloxycarbonyl glycine allyl ester (2) as a yellow oil: yield 242 mg (97%); $^1H$ NMR (CDCl) δ4.02 (d, 2H, J=5.8 Hz), 4.66 (d, 2H, J=5.8 Hz), 5.13–5.36 (m, 4H), 5.81–5.96 (m, 1H), 7.37 (s, 5H); mass spectrum (CI, methane) m/z 250 (M+H), 206, 91.

N-Benzyloxycarbonyl-2-Amino-4-Pentenoic Acid (3) To a cooled (−78° C.) solution of 103 mg (0.42 mmol) N-benzyloxycarbonyl glycine allyl ester (2) and 63 mg (0.46 mmol) $ZnCl_2$ in 1 mL THF was added 2.1 mL of a 1 M solution of lithium hexamethyldisilazane in THF. The mixture was stirred for 17 h, allowing the temperature to rise to rt. Ether (25 mL) was added and the solution was washed with two 25-mL portions of 1 M $NaHSO_4$. The organic phase was extracted with three 15-mL portions of saturated aqueous $NaHCO_3$, the aqueous layer acidified to pH 1 with solid $NaHSO_4$ and extracted with 3 20-mL portions of ether. The combined organic extracts were dried ($MgSO_4$) and concentrated. The crude material was applied to a silica gel column (1×22 cm) and elution with 8% MeOH and 1% AcOH in $CH_2cl_2$ gave N-benzyloxycarbonyl-2-amino-4-pentenoic acid (3) as a colorless oil: yield 26 mg (25%); $^1H$ NMR (CDCl$_3$) δ2.56–2.63 (m, 2H), 4.45–4.59 (m, 1H), 5.13–5.29 (m, 4H), 5.63–5.82 (m, 1H), 7.36 (s, 5H); mass spectrum (CI, methane) m/z 250 (M+H)+, 206, 91.

N-(N-Benzyloxycarbonyl-2-Amino-4-Pentenoyl)-L-Valine Benzxyl Ester (4) To a cooled (0–5° C.) solution of 24 mg (0.096 mmol) N-(N-benzyloxycarbonyl-2-amino-4-pentenoic acid (3), 36 mg (0.096 mmol) valine benzyl ester p-toluenesulfonyl salt, and 11 μL (0.096 mmol) N-methylmorpholine in 2 mL $CH_2Cl_2$ was added 14 mg (0.101 mmol) HOBt and 21 mg (0.101 mmol) DCC and the mixture was stirred for 19 h. The solution was filtered and the filtrate diluted with 10 mL $CH_2Cl_2$ and washed with two 10-mL portions of 0.5 N HCl, with two 10-mL portions of saturated aqueous $NaHCO_3$, and with 10 mL brine. The organic phase was dried ($MgSO_4$) and concentrated. The crude product was applied to a silica gel column (1×15 cm) and elution with 5% MeOH in $CH_2Cl_2$ gave pure N-(N-benzyloxycarbonyl-2-amino-4-Pentenoyl)-L-valine benzyl ester (4) as a colorless oil: yield 35 mg (83%); $^1H$ NMR (CDCl$_3$) δ0.80–0.90 (m, 6H); 2.14–2.20 (m, 1H); 2.49–2.56 (m, 2H); 4.20–4.32 (M, 1H); 4.55–4.60 (m, 1H0; 5.07–5.30 (M, 6H); 5.65–5.83 (m, 1H); 6.42–6.49 (m, 1H); 7.30–7.34 (m, 10H); mass spectrum (CI, methane) m/z 439 (M+H)+, 225.

L-Valine benzyl ester (5) (Deprotection compound 4) To a solution of 17.6 mg (0.040 mmol) N-(N-benzyloxycarbonyl-2-amino-4-pentenoyl)-valine benzyl ester (4) in 1 mL 1:1 THF-$H_2O$ was added 0.8 mL of a 0.25 M solution of $I_2$ in THF-$H_2O$. After 20 min solid $Na_2S_2O_3$ was added to quench the reaction and the solvent was removed under reduced pressure. The residue was suspended in 5% MeOH in $CH_2Cl_2$ and applied to a silica gel column (1×20 cm). Elution with 5% MeOH in $CH_2Cl_2$ gave valine benzyl ester (5) as a colorless oil: yield 5 mg (60%); $^1H$ NMR (CDCl$_3$) δ0.92 (d, 3H, J=6.9 Hz); 0.99 (d, 3H, J=6.9 Hz); 2.10–2.20 (m, 1H); 3.53 (d, 1H, J=4.2 Hz); 5.10–5.22 (m, 2H); 7.36 (s, 5H); mass spectrum (CI, methane) m/z 208 (M+H)+, 91.

N-butyloxycarbonyl-L-2-Amino-4-Pentenoic acid (7) To a cooled (0–5° C.) solution of 500 mg (4.34 mmol) 2-amino-4-pentenoic acid (6) in 10 mL dioxane, 5 mL $H_2O$ and 5 mL 1 M $NaHCO_3$ was added 1.10 g (5.04 mmol) di-t-butyl pyrocarbonate. The reaction was stirred for 19 h at room temperature. Water (20 mL) was added and the solution washed with two 25-mL portions of ether, acidified to pH 1 with 1 N $H_2SO_4$ and extracted with 3 20-mL portions of $CHCl_3$. The organic extracts were dried ($MgSO_4$) and concentrated to give N-butyloxycarbonyl-2-amino-4-pentenoic acid (7) as a colorless oil in quantitative yield: $_1H$ NMR (CDCl$_3$) δ1.45 (s, 9H); 2.55–2.61 (m, 2H); 4.35–4.45 (m, 1H); 4.95–5.10 (br, 1H); 5.15–5.21 (m, 2H); 5.68–5.81 (m, 1H); mass spectrum (CI, methane) m/z 216 (M+H)+, 160, 116.

N-(N-Butyloxycarbonyl-2-Amino-4-Pentenoyl)-L-Valine Benzyl Ester (8) To a solution of 275 mg (1.28 mmol) N-butyloxycarbonyl-2-amino-4-pentenoic acid (7) in 5 mL $CH_2Cl_2$ was added a solution of 486 mg (1.28 mmol) L-valine benzyl ester p-toluenesulfonate and 141 μL (1.28 mmol) N-methyl morpholine in 5 mL $CH_2Cl_2$. The solution was cooled in an icebath and 277 mg (1.34 mmol) DCC and 182 mg (1.34 mmol) HOBt were added. The mixture was stirred for 20 h and filtered. The filtrate was diluted with 20 mL $CH_2,Cl_2$ and washed with two 30-mL portions of 0.5 N HCl, with two 30-mL portions of saturated aqueous $NaHCO_3$ and with 30 mL brine. The organic phase was dried ($MgSO_4$) and concentrated. The crude product was applied to a silica gel column (2×20 cm) and elution with 3% MeOH in CH2Cl2 gave N-(N-butyloxycarbonyl-2-amino-4-pentenoyl)-L-valine benzyl ester (8) as a colorless oil: yield 428 mg (83%); $^1H$ NMR (CDCl$_3$) δ0.83–0.94 (m, 6H); 1.44 (s, 9H); 2/13–2.24 (m, 1H); 2.48–2.55 (m, 2H); 4.11–4.16 (m, 1H): 4.55–4.61 (m, 1H); 5.10–5.23 (m, 4H); 5.69–5.77 (m, 1H); 6.59–6.62 (m, 1H); 7.35 (s, 5H); mass spectrum (CI, methane) m/z 405 (M+H)+, 349, 305.

L-Valine Benzyl Ester (5) (Deprotection compound 8) To a solution of 26 mg ( ) 0.063 mmol) N-(N-butyloxycarbonyl-2-amino-4-pentenoyl)-L-valine benzyl ester (8) in 1 mL THF was added 1 mL $H_2O$ and a few drops THF until the solution was clear. 48 mg (0.19 mmol) $I_2$ was added and the reaction stirred for 7 min. The reaction was quenched with solid $Na_2S_2O_3$ and concentrated under reduced pressure. The residue was partitioned between 10 mL $CHCl_3$ and 10 mL saturated NaCl. The layers were separated and the organic layer was dried ($MgSO_4$) and concentrated. The residue was applied to a silica gel column (1×22 cm) and elution with 4% MeOH in $CH_2Cl_2$ gave valine benzyl ester (5) as a colorless oil: yield 4.7 mg (36%); $^1H$ NMR ($CDCl_3$) δ0.97 (d, 3H, J=6.9 Hz); 0.99 (d, 3H, J=6.6 Hz); 2.02–2.14 (m, 1H); 3.40 (d, 1H, J=5.0 Hz); 5.12–5.21 (m, 2H); 7.36 (s, 5H).

N-Phenylfluorenyl-2-Amino-4-Pentenoic acid (9) To a suspension of 115 mg (1 mmol) 2-amino-4-pentenoic acid (6) in 2 mL anhydrous $CH_2Cl_2$ was added 140 μL (1.1 mmol) Et3N was added and the mixture stirred for 15 min. 223 mg (0.67 mmol) $Pb(NO_3)_2$ was added, followed by 427 mg (1.33 mmol) 9-bromo-9-phenylfluorene and the reaction was stirred for 2 days. The mixture was filtered over celite and concentrated. The residue was dissolved in 20 mL $CH_2Cl_2$ and washed with two 20-mL portions of 5% citric acid and with 20 mL brine. The organic phase was dried ($MgSO_4$) and concentrated. The crude product was applied to a silica gel column (2×15 cm) and elution with 3% MeOH in $CH_2Cl_2$ gave N-phenylfluorenyl-2-amino-4-pentenoic acid (9) as colorless oil: yield 175 mg (49%); $^1H$ NMR ($CDCl_3$) δ1.93–2.02 (m, 1H); 2.41–2.49 (m, 1H); 2.72 (t, 1H, J=5.0 Hz); 5.13–5.23 (m, 2H); 5.43–5.53 (m, 1H); 7.19–7.76 (m, 13H); mass spectrum (CI, methane) m/z 356 (M+H)+, 241, 101.

N-(N-Phenylfluorenyl-2-Amino-4-Pentenoyl)-L-Valine Benzyl Ester (10) To a cooled (0–5° C.) solution of 58 mg (0.16 mmol) N-phenylfluorenyl-2-amino-4-pentenoic acid (9) in 2 mL $CH_2Cl_2$ was added 37 mg (0.18 mmol) DCC and 25 mg (0.18 mmol) HOBt. The mixture was stirred for 15 min and a solution of 62 mg (0.16 mmol) L-valine benzyl ester p-toluenesulfonate and 18 μL (0.16 mmol) N-methyl morpholine in 1 mL $CH_2Cl_2$ was added. The reaction was stirred for 17 h at room temperature. The mixture was filtered and the filtrate diluted with 10 mL $CH_2Cl_2$ and washed with two 10-mL portions of 0.5 N HCl, with two 10-mL portions of 0.5 N HCl, with two 10-mL portions of saturated aqueous $NaHCO_3$ and with 10 mL brine. The organic phase was dried ($MgSO_4$) and concentrated. The crude product was applied to a silica gel column (1×15 cm) and elution with 7:3 hexanes-EtOAc gave N-(N-phenylfluorenyl-2-amino-4-pentenoyl)-L-valine benzyl ester (10) as a colorless oil: yield 72 mg (81%); $^1H$ NMR ($CDCl_3$) μ 0.91–0.94 (m, 6H); 1.95–1.99 (m, 1H); 2.14–217 (m, 1H); 2.36–2.41 (m, 1H); 2.65–2.83 (m, 1H); 4.4–4.46 (m, 1H) 5.05–5.13 (m, 2H); 5.21–5.31 (m, 2H); 5.41–5.47 (m, 1H); 6.88 (t, 1H, J=7.7 Hz); 7.18–7.71 (m, 17H); 8.17 (d, 1H, J=8.5 Hz); mass spectrum (CI, methane) m/z 545 (M+H)+.

Iodolactone 11 and L-Valine Benzyl Ester (5) (Deprotection compound 10) To a solution of 33 mg (0.061 mmol) N-(N-phenylfluorenyl-2-amino-4-pentenoyl)-L-valine benzyl ester (10) in 1 mL THF was added 1 mL $H_2O$ and a few drops THF until the solution was clear. 77 mg (0.30 mmol) $I_2$ was added and the mixture stirred for 7 min. The reaction was quenched with solid $Na_2S_2O_3$ and concentrated under diminished pressure. The residue was dissolved in 10 mL $CH_2Cl_2$ and washed with two 10-mL portions of saturated aqueous $NaHCO_3$. The organic layer was dried ($MgSO_4$) and concentrated. The residue was applied to a silica gel column (1×10 cm) and elution with 1–5% MeOH in $CH_2Cl_2$ afforded the iodolactone 11 (13.4 mg, 46%) and valine benzyl ester (5) (9 mg, 71%): Iodolactone 11 $^1H$ NMR ($CDCl_3$) δ1.41–1.60 (m, 2H); 3.01–3.26 (m, 3H); 3.91–3.99 (m, 1H); 7.20–7.75 (m, 13H)); mass spectrum (CI, methane) m/z 481, 482 (M+H)+, 241; valine benzyl ester (5) $^1H$ NMR (CDCl3) δ0.88 (d, 3H, J=6.9 Hz); 0.96 (d, 3H, J=6.9 Hz); 2.00–2.10 (m, 1H); 3.34 (d, 1H, J=5.0 Hz); 5.16 (s, 2H); 7.36 (s, 5H); mass spectrum (CI, methane) m/z 208 (M+H)+

N-Phenylfluorenyl-L-2-Amino-4-Pentenoic acid (13) To a suspension of 75 mg (0.65 mmol) L-2-amino-4-pentenoic acid (12) in 2 mL anhydrous $CH_2Cl_2$ was added 120 μL (0.95 mmol) TMS-Cl. After stirring for 2 h at room temperature 132 μL (0.95 mmol) $Et_3N$ was added and the mixture stirred for 15 min. 136 mg (0.41 mmol) Pb ($NO_3)_2$ was added, followed by 278 mg (0.87 mmol) 9-bromo-9-phenyfluorene and the reaction was stirred for 3 days. The mixture was filtered over celite and concentrated. The residue waqs dissolved in 20 mL $CH_2Cl_2$ and washed with two 20-mL portions of 5% citric acid and with 20 mL brine. The organic phase was dried ($MgSO_4$) and concentrated. The crude product was applied to a silica gel column (2×15 cm) and elution with 3% MeOH in $CH_2Cl_2$ gave N-phenylfluorenyl-L-2-amino-4-pentenoic acid (13) as colorless oil: yield 135 mg (58%); silica gel TLC $R_f$ 0.3 (3% MeOH in $CH_2Cl_2$); $^1H$ NMR ($CDCl_3$) δ1.94–2.03 (m, 1H); 2.40–2.49 (m, 1H); 2.70 (t, 1H, J=5.4 Hz); 5.12–5.23 (m, 2H); 5.43–5.54 (m, 1H); 7.19–7.76 (m, 13H); mass spectrum (CI, methane) m/z 356 (M+H)+, 241.

N-(N-Phenylfluorenyl-L-2-Amino-4-Pentenoyl)-L-Phenylalanine Benzyl Ester (15) To a solution of 20 mg (0.055 mmol) N-phenylfluorenyl-L-2-amino-4-pentenoic acid (13) in 1 mL $CH_2Cl_2$ was added a solution fo 25 mg (0.058 mmol) L-phenylalanine benzyl ester p-toluenesulfonate and 6.5 μL (0.058 mmol) N-methyl morpholine in 1 mL $CH_2Cl_2$. The mixture was cooled in an icebath, 13 mg (0.063 mol) DCC and 8 mg (0.059 mmol) HOBt were added and the reaction was stirred for 20 h at room temperature. The mixture was filtered and the filtrate diluted with 10 mL $CH_2Cl_2$ and washed with two 10-mL portions of 0.5 N HCl, with two 10-mL portions of saturated aqueous $NaHCO_3$ and with 10 mL brine. The organic phase was dried ($MgSO_4$) and concentrated. The crude product was applied to a silica gel column (1×15 cm) and elution with 2% MeOH in $CH_2Cl_2$ gave N-(N-phenylfluorenyl-L-2-amino-4-pentenoyl)-L-phenylalanine benzyl ester (15) as a colorless oil that solidified upon standing: yield 27 mg (83%); silica gel TLC $R_f$ 0.74 (1:1 ethyl acetate-hexanes); $^1H$ NMR ($CDCl_3$) δ1.83–1.95 (m, 1H); 2.25–2.35 (m, 1H); 2.52–2.58 (m, 1H); 3.01–3.18 (m, 2H); 4.72–4.79 (m, 1H); 5.01–5.10 (m, 2H); 5.20 (s, 2H); 5.25–5.38(m, 1H); 6.88–8.00 (m, 23H).

N-(N-phenylfluorenyl-L-2-Amino-4-Pentenoyl)-DL-Phenylalanine Benzyl Ester (14 and 15) To a solution of 18 mg (0.052 mmol) N-phenylfluorenyl-L-2-amino-4-pentenoic acid (13) in 1 mL $CH_2Cl_2$ was added a solution of 23 mg (0.055 mmol) DL-phenylalanine benzyl ester p-toluenesulfonate and 6 μL (0.055 mmol) N-methylmorphoneline in 1 mL $CH_2Cl_2$. The mixture was cooled in an icebath, 12 mg (0.058 mmol) DCC and 8 mg (0.059 mmol) HOBt were added and the reaction was stirred for 22 h at room temperature. The mixture was filtered and the filtrate diluted with 10 mL $CH_2Cl_2$ and washed with two 10-mL portions of 0.5 N HCl, with two 10-mL portions of saturated aqueous $NaHCO_3$ and with 10 mL brine. The organic phase was dried ($MgSO_4$) and concentrated. The crude product was applied to a silica gel column (1×12 cm) and elution with 2% MeOH in $CH_2Cl_2$ gave N-(N-phenylfluorenyl-L-2-amino-4-pentenoyl)-DL-phenylalanine benzyl ester (14 and 15 mixture of diastereomers) as a colorless oil: yield 30 mg (97%);silica gel TLC $R_f$ 0.74 (1:1 ethyl acetate-hexanes); $^1$H NMR ($CDCl_3$) δ1.80–1.96 (m, 1H); 2.23–2.42 (m, 1H); 2.48–2.58 (m, 1H); 3.05–3.18 (m, 2H); 4.53–4.59 (m, 0.5H); 4.75–4.81 (m, 0.5H); 5.05–5.16 (m, 2H); 5.20–5.57 (m, 3H); 6.86–7.71 (m, 23H).

Separation of 14 and 15 by HPLC. The mixture of diastereomers 14 and 15 was dissolved in 4 mL 4:1 hexanes-ethyl acetate and analyzed by HPLC. A 10 μL aliquot was diluted with 70 μL 4:1 hexanes-ethyl acetate and injected on a Partisil silica column (250×10 mm). Elution was performed with a gradient of 5–25% ethyl acetate in hexanes n 30 min at a flowrate of 3.5 mL/min. Detection was at 275 nm. Two major peaks were found at 26.2 min and 26.8 min in a 40–60 ratio. Coinjection with compound 15 derived from optically pure L-phenylalanine benzyl ester showed that the peak at 26.8 min was the L-amino acid derivative.

N-Butyloxycarbonyl-L-2-Amino-4-Pentenoic acid (16) To a solution of 230 mg (1 mmol) L-2-amino-4-pentenoic acid (12) in 5 mL dioxane, 2.5 mL $H_2O$ and 2.5 mL 1 M $NaHCO_3$ was added 480 mg (2.2 mmol) di-t-butyl pyrocarbonate. The reactionn was stirred for 15 h at rt. Water (20 mL) was added and the solution was washed with two 25-mL portions of ether, acidified to pH 1 with 1 N $H_2SO_4$ and extracted with 3–20 mL portions of $CH_2Cl_2$. The organic extracts were dried ($MgSO_4$) and concentrated to give N-butyloxycarbonyl-L-2-amino-4-pentenoic acid (16) as a colorless oil in quantitative yield: $^1$H NMR ($CDCl_3$) δ1.45 (s, 9H); 2.52–2.61 (m, 2H); 4.35–4.45 (m, 1H); 4.95–5.10 (br, 1H); 5.15–5.21 (m, 2H); 5.67–5.81 (m, 1H); mass spectrum (CI, methane) m/z 216 (M+H)$^+$, 431, 160.

O-Nitrobenzyl N-Butyloxycarbonyl-L-2-Amino-4-Pentenoate (17) To a solution of 430 mg (2 mmol) N-butyloxycarbonyl-L-2-amino-4-pentenoic acid (16) in 4 mL ethyl acetate was added 4 mL of a 0.5 N solution of $CS_2CO_3$ in $H_2O$. The mixture was stirred for 10 min, 4 mL toluene was added and the solvent removed under diminished pressure. Another 4 mL portion of toluene was added and removed under disminished pressure. The residue was dissolved in 10 mL anhydrous DMF and 432 mg (2 mmol) o-nitrobenzyl bromide was added. The reaction was stirred for 17 h and DMF was removed under diminished pressure. The residue was dissolved in 50 mL $CH_2Cl_2$ and washed with two 50-mL portions of water and with 50 mL brine. The organic phase was dried ($MgSO_4$) and concentrated. The crude product was purified by flash column chromatography on a silica gel column (2×25 cm). Elution with 2% MeOH in $CH_2Cl_2$ gave pure o-nitrobenzyl 1N-butyloxycarbonyl-L-2-amino-4-pentenoate (17) as a yellow oil: yield 672 mg (96%); $^1$H NMR ($CDCl_3$) δ1.44 (s, 9H); 2.53–2.59 (m, 2H); 4.38–4.48 (m, 1H); 5.02 (br, 1H); 5.12–5.18 (m, 2H); 5.58 (s, 2H); 5.63–5.78 (m, 1H); 7.48–7.53 (m, 1H); 7.60–7.70 (m, 2H); 8.09–8.14 (m, 1H); mass spectrum (CI, methane) m/z 351 (M+H)$^+$, 295, 251, 136.

O-Nitrobenzyl-L-2-Amino-4-Pentenoate (18) To a cooled (0–5° C.) solution of 338 mg (0.96 mmol) o-nitrobenzyl N-butyloxycarbonyl-L-2-amino-4-pentenoate (17) in 5 mL freshly distilled $CH_2Cl_2$ was added 0.75 mL (9.7 mmol) TFA. The mixture was stirred for 2 h. Toluene (5 mL) was added and the solvent removed under diminished pressure. Another 5 mL portion of toluene was added and the solution concentrated. The residue was dissolved in 30 mL $CH_2Cl_2$ and washed with two 30-mL portions of saturated aqueous $NaHCO_3$. The organic phase was dried ($MgSO_4$) and concentrated to give o-nitrobenzyl-L-2-amino-4-pentenoate (18) as a colorless oil: yield 234 mg (97%); $^1$H NMR (CDCl3) δ2.39–2.61 (m, 2H); 3.65–3.69 (m, 1H); 5.10–5.19 (m, 2H); 5.56 (s, 2H); 5.68–5.82 (m, 1H); 7.49–7.68 (m, 3H); 8.11 (d, 1H. J=8.1 Hz); mass spectrum (CI, methane) m/z 251 (M+H)$^+$, 501, 136.

O-Nitrobenzyl-N-Benzyl-L-2-Amino-4-Pentenoate (19) To a solution of 230 mg (0.92 mmol) o-nitrobenzyl-L-2-amino-4-pentenoate (18) in 5 mL MeOH was added 76 μL conc. HCl. Toluene (4 mL) was added and the solution concentrated under reduced pressure.

The residue was dissolved in 5 mL MeOH and 58 mg (0.92 mmol) $NaBH_3CN$ was added, followed by 94 μL (0.92 mmol) benzaldehyde. The mixture was stirred for 15 h at room temperature, acidified to pH 1 with conc. HCl and stirred for anther hour. MeOH was removed and the residue dissolved in a minimal amount of water. The pH was adjusted to 10 with saturated aqueous $Na_2CO_3$ and the solution extracted with 3–15 mL portions of $CH_2Cl_2$. The combined extracts were dried ($MgSO_4$) and concentrated. The crude product was applied to a silica gel column (2×25 cm) and elution with 2% MeOH in $CH_2Cl_2$ gave o-nitrobenzyl-N-benzyl-L-2-amino-4-pentenoate (19) as a colorless oil: yield 133 mg (42%); $^1$H NMR ($CDCl_3$) δ2.48 (t, 2H, J=7.2 Hz); 3.47 (t, 1H, J=6.5 Hz); 3.78 (dd, 2H, J=36.6 Hz, J=13.1 Hz); 5.06–5.14 (m, 2H); 5.49–5.60 (m, 2H); 5.69–5.83 (m, 1H); 7.23–7.33 (m, 5H); 7.49–7.68 (m, 3H); 8.11 (d, 1H, J=6.9 Hz); mass spectrum (CI, methane) m/z 3341 (M+H)$^+$.

O-Nitrobenzyl-N-Benzyl-N-Phenylfluorenyl-L-2-Amino-4-Pentenoate (20) To a solution of 130 mg (0.38 mmol) o-nitrobenzyl-N-benzyl-L-2-amino-4-pentenoate (19) in 5 mL anhydrous $CH_3CN$ was added 154 mg (0.48 mmol) 9-bromo-9-phenylfluorene, followed by 90 mg (0.42 mmol) $K_3PO_4$ and 100 mg (0.30 mmol) $Pb(No_3)_2$. The mixture was stirred for 3 days, filtered over celite and concentrated under diminished pressure. The residue was dissolved in 20 mL $CH_2Cl_2$ and washed with two 20-mL portions of 5% citric acid and with 10 mL brine. The organic phase was dried ($MgSO_4$) and concentrated. The crude product was applied to a silica gel column (2×20 cm) and elution with 4:1 hexanes-EtOAc gave o-nitrobenzyl-N-benzyl-N-phenylfluorenyl-L-2-amino-4-pentenoate (20) as a colorless foam: yield 204 mg (92%); $^1$H NMR (CDCl$_3$) δ1.73–1.82 (m, 1H); 2.17–2.26 (m, 1H); 3.38–3.43 (m, 1H); 4.13 (d, 1H, J=14.3 Hz); 4.44 (d, 1H, J=14.3 Hz); 4.50 (d, 1H, J=18.9 Hz); 4.67 (d, 1H, J=10.0 Hz); 4.72 (d, 1H, J=15.4 Hz); 5.05 (d, 1H, J=15.4 Hz); 5.24–5.30 (m, 1H); 7.17–7.77 (m, 21H); 8.09 (d, 1H, J=8.1 Hz); mass spectrum (CI, methane) m/z 581 (M+H)$^+$, 241.

N-Benzyl-N-Phenylfluorenyl-L-2-Amino-4-Pentenoic Acid (21) A solution of 110 mg (0.19 mmol) o-nitrobenzyl-N-benzyl-N-phenylfluorenyl-L-2-amino-4-pentenoate (20) in 1 mL THF was divided over two plastic tubes. Each tube was irradiated with a 500 W xenon-mercury lamp for 1 hour at 2° C. The fractions were combined and concentrated under reduced pressure. The residue was dissolved in 20 mL CH$_2$Cl$_2$ and washed with two 20-mL portions of 0.5 N HCl. The organic phase was dried (MgSO$_4$) and concentrated. The crude product was applied to a silica gel column (2×12 cm) and elution 4:1 hexanes-EtOAc afforded N-benzyl-N-phenylfluorenyl-L-2-amino-4-pentenoic acid (21) as a yellow oil: yield 29 mg (34%); $^1$H NMR (CDCl$_3$) δ1.63–1.69 (m, 1H); 2.37–2.47 (m, 1H); 3.08–3.12 (m, 1H); 4.00 (d, 1H, J=13.5 Hz); 4.38 (d, 1H, J=13.1 Hz); 4.40 (d, 1H J=18.5 Hz); 4.63 (d, 1H, J=10.0 Hz); 5.29–5.40 (m, 1H); 7.19–7.82 m, 18H). N-(N-Benzyl-N-Phenylfluorenyl-L-2-Amino-4-Pentenoyl)-DL-Valine Bensyl ester (22 and 23) To a solution of 53 mg (0.12 mmol) N-benzyl-N-phenylfluorenyl-L-2-amino-4-pentenoic acid (21) in 1 mL CH$_2$Cl$_2$ was added a solution of 56 mg (0.15 mmol) DL-valine benzyl ester p-toluenesulfonate in 1 mL pyridine. To the solution was added 31 mg (0.15 mmol) DCC and the mixture was stirred for 19 h. The solvent was removed under reduced pressure. The residue was dissolved in 10 mL CH$_2$Cl$_2$, filtered, and washed with two 10-mL portions of 0.5 N HCl, two 10-mL portions of saturated aqueous NaHCO$_3$ and with 10 mL brine. The organic phase was dried (MgSO$_4$) and concentrated. The residue was applied to a silica gel column (2×25 cm) and elution with 4:1 hexanes-ethyl acetate gave two major products: N-(N-benzyl-N-phenylfluorenyl-L-2-amino-4-pentenoyl)-D-valine benzyl ester (22) as a colorless oil that solidified upon standing: yield 15 mg (20%); silica gel TLC R$_f$ 0.45 (4:1 hexanes-ethyl acetate); $^1$H NMR (CDCl$_3$) δ0.64 (d, 3H, J=6.9 Hz); 0.75 (d, 3H, J=6.9 Hz); 1.39–1.47 (m, 1H); 1.92–2.01 (m, 1H); 2.44–2.58 (m, 1H); 2.87 (d, 1H, J=10.0 Hz); 3.69–3.73 (m, 1H); 3.91 (d, 1H, J=13.1 Hz); 4.26–4.33 (m, 2H); 4.54 (d, 1H, J=10.0 Hz); 5.30–5.45 (M, 3H); 6.98–7.81 (m, 23H); mass spectrum (CI, methane) m/z 635.7 (M+H)$^+$, 241.1, and N-(N-benzyl-N-phenylfluorenyl-L-2-amino-4-pentenoyl)-L-valine benzyl ester (23) as a colorless oil: yield 33 mg (44%); silica gel TLC R$_f$ 0.39 (4:1 hexanes-ethyl acetate); $^1$H NMR (CDCl$_3$) δ0.66 (d, 3H, J=6.9 Hz); 0.71 (d, 3H, J=6.9 Hz); 1.56–1.64 (m, 1H); 1.86–1.93 (m, 1H); 2.41–2.50 (m, 1H); 3.03–3.07 (m, 1H); 4.04–4.09 (m, 2H); 4.27 (d, 1H, J=13.9 Hz); 4.48 (d, 1H, J=17.3 Hz); 4.62 (d, 1H, J=10.0 Hz); 5.19 (d, 2H, J=4.2 Hz); 5.25–5.35 (m, 1H); 6.97–7.78 (m, 23H); mass spectrum (CI, methane) m/z 635.6 (M+H)$^+$, 241.2.

N-(N-Benzyl-N-Phenylfluorenyl-L-2-Amino-4-Pentenoyl)-D-Valine Benzyl ester (22) To a solution of 14 mg (0.0.31 mmol) N-benzyl-N-phenylfluorenyl-L-2-amino-4-pentenoic acid (21) in 0.5 mL CH$_2$Cl$_2$ was added a solution of 23 mg (0.061 mmol) D-valine benzyl ester p-toluenesulfonate in 0.5 mL pyridine. To the solution was added 8 mg (0.0.41 mmol) DCC and the mixture was stirred for 17 h. The solvent was removed under reduced pressure. The residue was dissolved in 10 mL CH$_2$Cl$_2$, and washed with two 10-mL portions of 0.5 N HCl, two 10-mL portions of saturated aqueous NaHCO$_3$ and with 10 mL brine. The organic phase was dried (MgSO$_4$) and concentrated. The residue was applied to a silica gel column (1×15 cm) and elution was 4:1 hexanes-ethyl acetate gave N-(N-benzyl-N-phenylfluorenyl-L-2-amino-4-pentenoyl)-D-valine benzyl ester (22) as a colorless oil that solidified upon standing: yield 11 mg (56%); silica gel TLC R$_f$ 0.45 (4:1 hexanes-ethyl acetate); $^1$H NMR (CDCl$_3$) δ0.64 (d, 3H, J=6.9 Hz); 0.75 (d, 3H, J=6.9 Hz); 1.40–1.48 (m, 1H); 1.92–2.00 (m, 1H); 2.46–2.56 (m, 1H); 2.88 (d, 1H, J=10.0 Hz); 3.70–3.73 (m, 1H); 3.91 (d, 1H, J=13.1 Hz); 4.27–4.33 (m, 2H); 4.54 (d, 1H, J=10.0 Hz); 5.27–5.46 (m, 3H); 6.98–7.82 (m, 23H).

N-(N-Benzyl-N-Phenylfluorenyl-L-2-Amino-4-Pentenoyl)-L-Valine Benzyl ester (23) To a solution of 17 mg (0.038 mmol) N-benzyl-N-phenylfluorenyl-L-2-amino-4-pentenoic acid (21) in 0.5 mL CH$_2$Cl$_2$ was added a solution of 29 mg (0.076 mmol) L-valine benzyl ester p-toluenesulfonate in 0.5 mL pyridine. To the solution was added 10 mg (0.048 mmol) DCC and the mixture was stirred for 20 h. The solvent was removed under reduced pressure. The residue was dissolved in 10 mL CH$_2$Cl$_2$, and washed with two 10-mL portions of 0.5 N HCl, two 10-mL portions of saturated aqueous NaHCO$_3$ and with 10 mL brine. The organic phase was dried (MgSO$_4$) and concentrated. The residue was applied to a silica gel column (1×20 cm) and elution with 4:1 hexanes-ethyl acetate gave N-(N-benzyl-N-phenylfluorenyl-L-2-amino-4-pentenoyl)-L-valine benzyl ester (23) as a colorless oil: yield 17 mg (70%); silica gel TLC R$_f$ 0.38 (4:1 hexanes-ethyl acetate); $^1$H NMR (CDCl$_3$) δ0.66 (d, 3H, J=6.9 Hz); 0.71 (d, 3H, J=6.9 Hz); 1.56–1.64 (m, 1H); 1.86–1.93 (m, 1H); 2.41–2.50 (m, 1H); 3.03–3.07 (m, 1H); 4.04–4.09 (m, 2H); 4.26 (d, 1H, J=13.5 Hz); 4.48 (d, 1H, J=17.3 Hz); 4.62 (d, 1H, J=10.0 Hz); 5.19 (d, 2H, J=4.2 Hz); 5.25–5.35 (m, 1H); 6.97–7.77 (m, 23H); mass spectrum (CI, methane) m/z 635.8 (M+H)$^+$, 241.2.

Separation of diastereomers 22 and 23 by HPLC. The crude mixture of diastereomers 22 and 23 derived from the reacion with racemic valine benzyl ester was dissolved in 5 mL 4:1 hexanes-ethyl acetate and analyzed by HPLC. A 10 μL aliquot was diluted with 70 μL 4:1 hexanes-ethyl acetate and injected on a Partisil silica column (250×10 mm). Elution was performed with a gradient of 5–25% ethyl acetate in hexanes in 30 min at a flowrate of 3.5 mL/min. Detection was at 275 nm. Two major peaks were found at 17.6 min and 21.3 min in a 1 to 2 ratio. Coinjection with compounds 22 and 23 derived from optically pure D- and L-valine benzyl ester, respectively, showed that the peak at 17.6 min was the diastereomer derived from the D-amino acid and the peak at 21.3 min the diastereomer that was derived from the L-amino acid.

Preparation of Misacylated tRNA

The use of the 4-pentenoyl group for the elaboration of processing a misacylated suppressor tRNA's employs the inventive protective group in the preparation of an amino acid di-nucleotide synthetic group:

N-(4-pentenoyl)valyl-pdCpA was prepared. Treatment of S-valine methyl ester with 4-pentenoic anhydride afforded the respective amide as a colorless oil in 73% yield. Following hydrolysis of the ester moiety (LiOH, aq THF), the derived intermediate was converted to the respective cyanomethyl ester (4). Admixture of 4 and pdCpA Robertson, et al., Nucleic Acids Res. 17:9649 (1989), in freshly distilled DMF afforded N-(4-pentenoyl)valyl-pdCpA (5) as a colorless solid in 94% yield. A sample of N-(2-nitroveratryloxycarbonyl)valyl-pdCpA was prepared as described, Robertson, et al., J. Am. Chem. Soc. 113:2722 (1991) for comparative purposes.

Deblocking of protected valyl-pdCpA derivatives was effected by treatment with iodine and hv irradiation. Hplc analysis of the reaction mixtures indicated complete deblocking of both compounds within 5 minutes to afford putative valyl-pdCpA.

Protected valyl-pdCpA's were each ligated to a suppressor tRNA transcript lacking the 3'-terminal pCpA moiety. N-(4-pentenoyl)valyl-tRNA was deprotected in aqueous THF containing 5 mM iodine; aliquots of the reaction mixture were employed in an in vitro protein biosynthesizing system in direct comparison with valyl-tRNA prepared by photodeprotection of N-(2-nitroveratryloxycarbonyl) valyl-tRNA. The synthesis of dihydrofolate reductase (DHFR) from a mRNA containing a nonsense codon at position 10 proceeded to the same extent from deblocked N-(4-pentenoyl)valyl-tRNA and (NVOC)valyl-tRNA; Robertson, et al., J. Am. Chem. Soc. 113:2722 (1991) no DHFR was obtained in the presence of the N-(4-pentenoyl) valyl-tRNA if iodine treatment was omitted. The use of aliquots of N-(4-pentenoyl)valyl-tRNA treated with iodine for varying lengths of time suggested that deprotecton was complete within 5–10 min. That the extent of DHFR production did not diminish when the activated tRNA was treated with iodine for up to 60 min is consistent with the lack of effect of iodine on the derived valyl-tRNA. Lindner, et al., Cromatographic Chiral Separations, page 91 (1988).

This establishes the feasibility of using the pentenoyl group for protection of the α-amino group during the synthesis of aminoacylated tRNA's. The availability of a chemically removable protecting group for $N^\alpha$ of the amino acid should also permit the elaboration of aminoacyl-tRNA's in which side chain functional groups of amino acids are protected differentially, such that deblocking can be effected subsequent to protein synthesis. This may, for example, facilitate the incorporation of charged amino acids such as aspartic acid, which has proved to be problematic. Skidmore, et al. Handbook of Derivatives for Chromatography, page 215 (1993).

Scheme 1

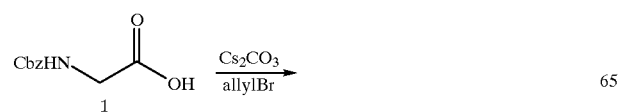

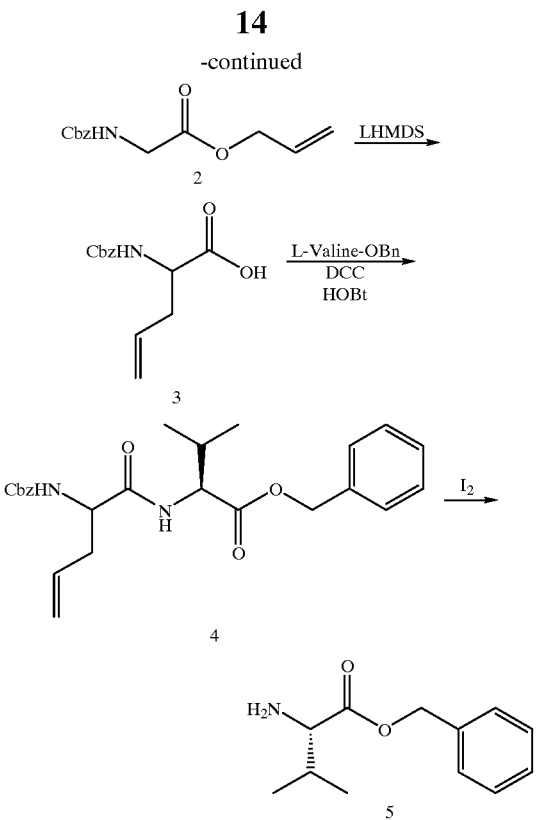

Scheme 3
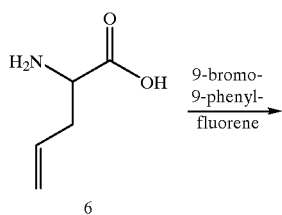
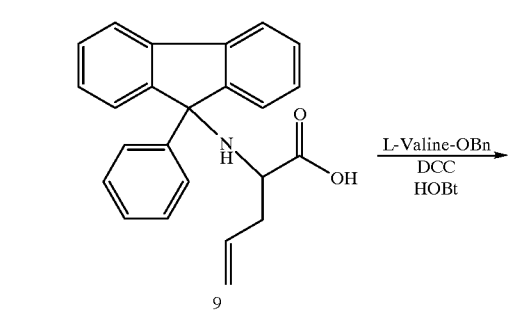
Scheme 4
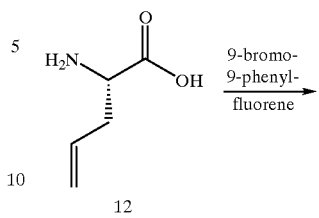
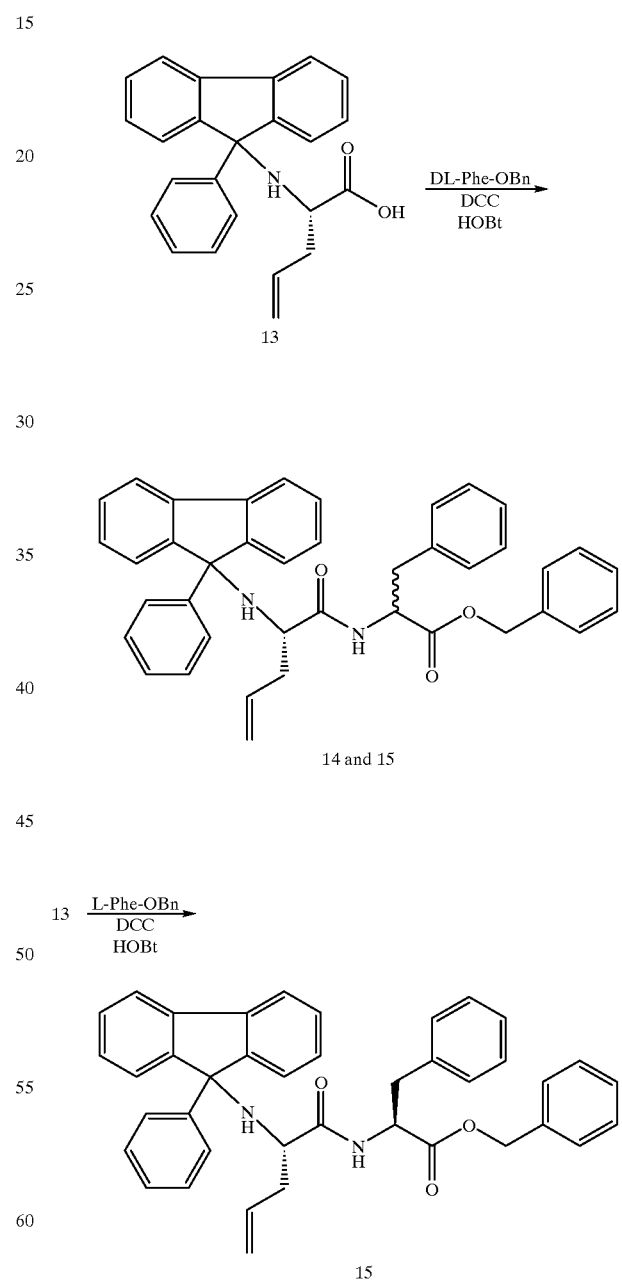

Scheme 5
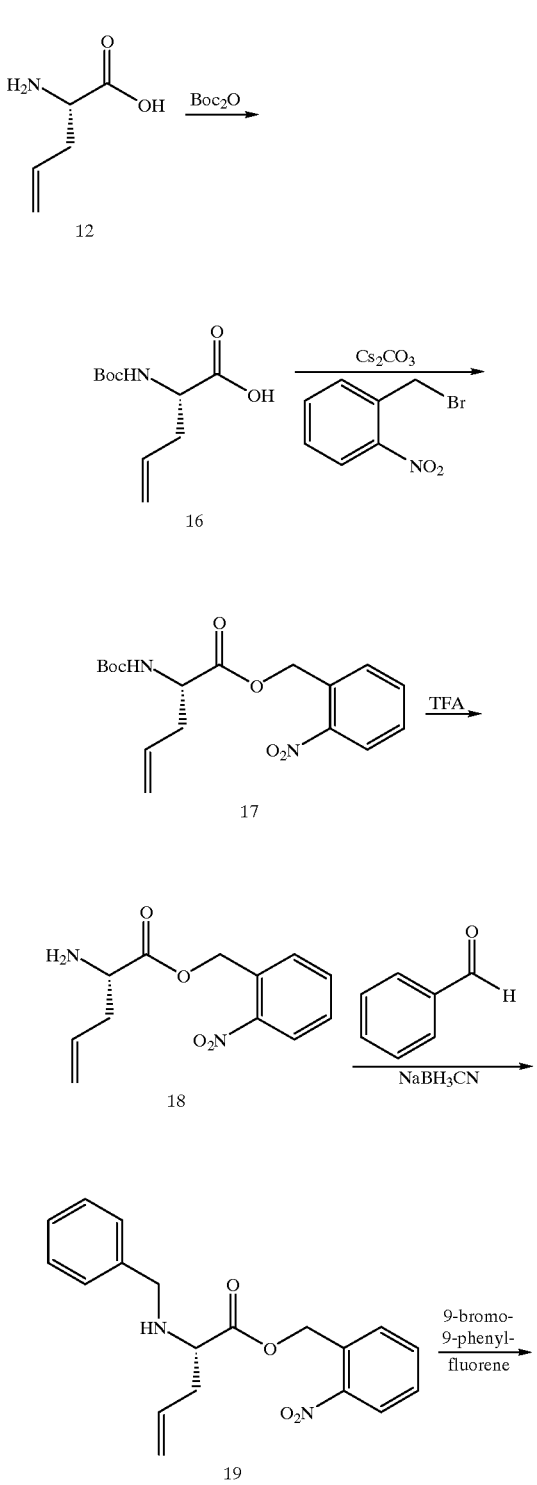
Scheme 6
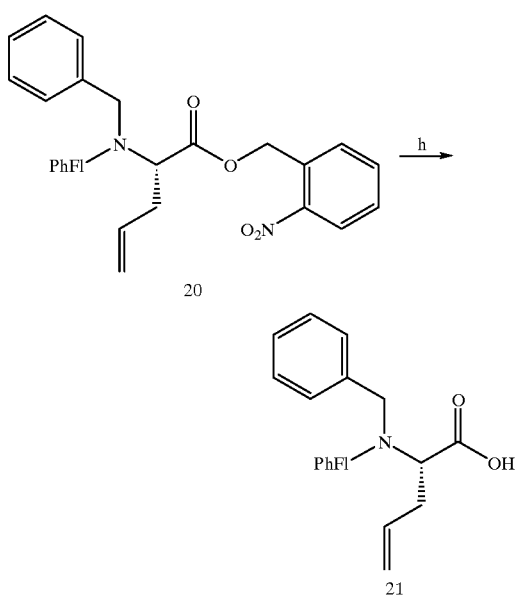
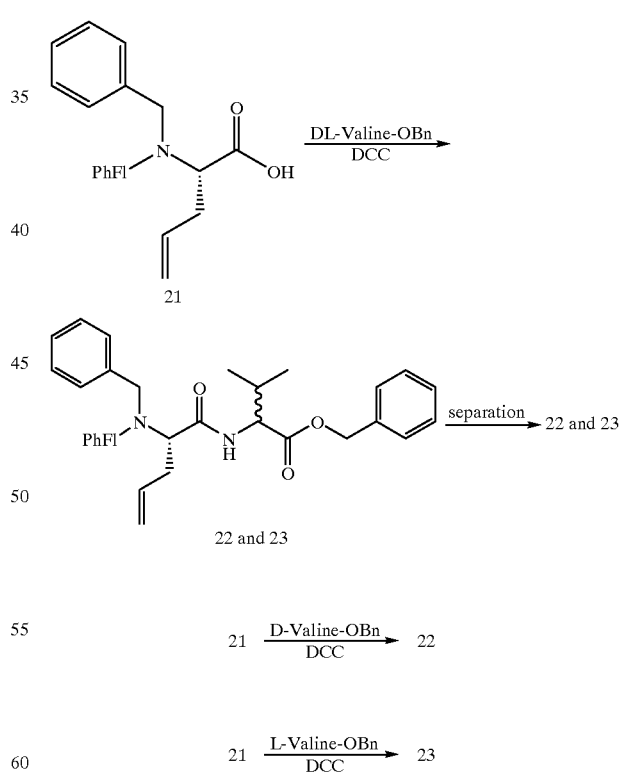

What is claimed is:

1. A compound of the formula (I):

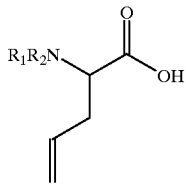

(I)

wherein $R_1$ is selected from the group consisting of aryl, aryloxy, carboxy, carbonyl, alkoxy, cyclic alkyl, fused and unfused polycyclic compounds, said $R_1$ having from 6 to 30 carbon atoms; or $R_1$ is butyloxycarbonyl; and $R_2$ is independently as defined for $R_1$; and wherein at least one of $R_1$ or $R_2$ is phenylfluorenyl.

2. The compound of claim 1, wherein $R_1$ is phenylfluorenyl, and $R_2$ is benzyl.

3. The compound of claim 1, wherein $R_1$ is butyloxycarbonyl.

4. The compound of claim 1, wherein $R_1$ is phenylfluorenyl, and $R_2$ is benzyloxycarbonyl, phenylfluorenyl or benzyl.

5. A compound which is N-phenylfluorenyl-L-2-amino-4-pentenoic acid.

6. A method of separating a racemic mixture of amino acid enantiomers, comprising reacting said mixture with a non-racemic compound of the formula:

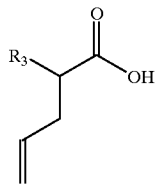

to form a protected form of the amino acid,
wherein $R_3$ is —$NR_1R_2$, wherein $R_1$ is selected from the group consisting of aryl, aryloxy carboxy, carbonyl, alkoxy, cyclic alkyl, fused and unfused polycyclic compounds, said $R_1$ having from 6 to 30 carbon atoms; or $R_1$ is butyloxycarbonyl; and $R_2$ is independently as defined for $R_1$ or H.

7. The method of claim 6, wherein at least one of $R_1$ or $R_2$ is phenylfluorenyl.

8. The method of claim 6, wherein $R_1$ is phenylfluorenyl, and $R_2$ is benzyl.

9. The method of claim 6, wherein at least one of $R_1$ or $R_2$ is butyloxycarbonyl.

10. The method of claim 6, wherein the non-racemic compound is N-phenylfluorenyl-L-2-amino-4-pentenoic acid.

11. A method of protecting an amino acid for subsequent attachment to a t-RNA, comprising reacting said amino acid with a compound of the following formula:

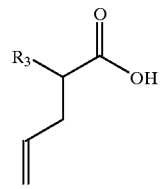

to form a protected form of the amino acid,
wherein $R_3$ is H or —$NR_1R_2$, wherein $R_1$ is selected from the group consisting of aryl, aryloxy, carboxy, carbonyl, alkoxy, cyclic alkyl, fused and unfused polycyclic compounds, said $R_1$ having from 6 to 30 carbon atoms; or $R_1$ is butyloxycarbonyl; and $R_2$ is H or independently as defined for $R_1$.

12. The method of claim 11, wherein in the formula $R_3$ is H.

13. The method of claim 11, wherein the formula $R_3$ is —$NR_1R_2$, and wherein at least one of $R_1$ or $R_2$ is phenylfluorenyl.

14. The method of claim 13, wherein $R_1$ is phenylfluorenyl and $R_2$ is benzyl.

15. The method of claim 11, wherein in the formula $R_3$ is $NR_1R_2$, and at least one of $R_1$ or $R_2$ is butyloxycarbonyl.

16. The method of claim 11, wherein the compound is N-phenylfluorenyl-L-2-amino-4-pentenoic acid.

17. A method of misacylating a t-RNA, comprising coupling one or more aminoacylated nucleotides with t-RNA from which the same number of 3'- terminal nucleotide groups have been removed, wherein said one or more aminoacylated nucleotides are protected with a compound of the formula:

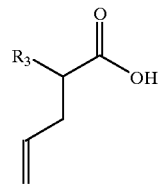

wherein $R_3$ is H or —$NR_1R_2$, wherein $R_1$ is selected from the group consisting of aryl, aryloxy, carboxy, cabonyl, alkoxy, cyclic alkyl, fused and unfused polycyclic compounds, said $R_1$ having from 6 to 30 carbon atoms; or $R_1$ is butyloxycarbonyl; and $R_2$ is H or independently as defined for $R_1$.

18. The method of claim 17, wherein said nucleotide group comprises 2 nucleotides, and said t-RNA has had an equal number of nucleotides removed from its 3'-terminal end.

19. The method of claim 17, herein said misacylated t-RNA is treated with aqueous iodine to remove the protective groups.

* * * * *